United States Patent
Almeida et al.

(10) Patent No.: US 8,960,071 B2
(45) Date of Patent: Feb. 24, 2015

(54) PISTON PUMP WITH LEAK DIAGNOSTIC PORT

(75) Inventors: Neal B. Almeida, Cumberland, RI (US);
Joshua A. Shreve, Franklin, MA (US);
John Angelosanto, North Attleboro, MA (US)

(73) Assignee: Waters Technologies Corporation, Milford, MA (US)

( * ) Notice: Subject to any disclaimer, the term of this patent is extended or adjusted under 35 U.S.C. 154(b) by 904 days.

(21) Appl. No.: 13/093,324

(22) Filed: Apr. 25, 2011

(65) Prior Publication Data
US 2012/0097026 A1    Apr. 26, 2012

Related U.S. Application Data

(60) Continuation-in-part of application No. 12/652,271, filed on Jan. 5, 2010, now Pat. No. 8,176,932, which is a division of application No. 11/573,742, filed as application No. PCT/US2005/029205 on Aug. 17, 2005, now Pat. No. 7,665,480.

(60) Provisional application No. 60/602,376, filed on Aug. 18, 2004.

(51) Int. Cl.
*F16J 15/18*    (2006.01)
*F04B 53/04*    (2006.01)
(Continued)

(52) U.S. Cl.
CPC .............. *F04B 53/04* (2013.01); *F04B 53/164* (2013.01); *F16J 15/004* (2013.01); *G01N 2030/326* (2013.01)
USPC ................................ 92/86; 92/168

(58) Field of Classification Search
CPC ............... F16J 15/004; F16J 15/182

USPC .............................. 277/320, 514; 92/86, 168
See application file for complete search history.

(56) References Cited

U.S. PATENT DOCUMENTS 706,536 A * 8/1902 Dougan et al. ................ 277/512
3,626,770 A * 12/1971 Lindberg et al. ............. 277/320
(Continued)

FOREIGN PATENT DOCUMENTS

| JP | 5215243 | 8/1993 |
| JP | 2001516846 | 10/2001 |

(Continued)

OTHER PUBLICATIONS

Translation of Notice of Rejection (Official Action) for Japanese Patent Applicatioon No. 2007-527964, dated Jul. 5, 2011.
(Continued)

*Primary Examiner* — F. Daniel Lopez
(74) *Attorney, Agent, or Firm* — Schmeiser, Olsen & Watts LLP

(57) ABSTRACT

Described are embodiments of a pump having a diagnostic port that enables users and support personnel to diagnose the source of a pump leak. The diagnostic port is monitored visually or with a pressure or liquid detection sensor. In some embodiments, fluid detected at the diagnostic port corresponds to a leak around a circumference defined at an outer sealing surface of a high pressure seal. In other embodiments, fluid detected at the diagnostic port corresponds to a leak around a plunger at the inside diameter of the high pressure seal. Multiple diagnostic ports can be provided to allow separate determinations of leaks about the different portions of the high pressure seal. The embodiments may eliminate the need to disassemble the pump to determine the source of leaks. Thus the effort required to diagnose and repair the pump can be substantially reduced, and fewer misdiagnosed components are ordered or replaced.

7 Claims, 4 Drawing Sheets

(51) Int. Cl.
*F04B 53/16* (2006.01)
*F16J 15/00* (2006.01)
*G01N 30/32* (2006.01)

(56) References Cited

U.S. PATENT DOCUMENTS

| | | |
|---|---|---|
| 4,398,727 A | 8/1983 | Rylander |
| 5,090,871 A | 2/1992 | Story et al. |
| 5,755,372 A * | 5/1998 | Cimbura ................. 277/320 |
| 5,788,465 A | 8/1998 | Luongo et al. |
| 5,941,530 A | 8/1999 | Williams |
| 6,000,422 A | 12/1999 | Shigemoto |
| 6,592,126 B2 * | 7/2003 | Davis ..................... 277/320 |
| 6,962,348 B2 | 11/2005 | Fink |
| 7,509,841 B2 | 3/2009 | Spaolonzi et al. |
| 2010/0163638 A1 * | 7/2010 | Herre et al. ............. 277/320 |

FOREIGN PATENT DOCUMENTS

| | | |
|---|---|---|
| JP | 2002039083 | 2/2002 |
| JP | 2006507462 | 3/2006 |

OTHER PUBLICATIONS

Translation of Official Action in related Japanese patent application No. 2007-527964, mailed on May 15, 2012; 2 pages.

* cited by examiner

PISTON PUMP WITH LEAK DIAGNOSTIC PORT

CROSS REFERENCE TO RELATED APPLICATIONS

This application is a continuation-in-part of U.S. patent application Ser. No. 12/652,271, filed on Jan. 5, 2010, which is a divisional of U.S. patent application Ser. No. 11/573,742, now U.S. Pat. No. 7,665,480, which entered the U.S. national stage on Aug. 22, 2007 as the U.S. national phase application of PCT international application No. PCT/US2005/029205, filed Aug. 17, 2005, which claims priority from U.S. Provisional Patent Application Ser. No. 60/602,376, filed Aug. 18, 2004. The entireties of these applications are incorporated herein by reference.

FIELD OF THE INVENTION

The invention relates generally to a pump for a liquid chromatography system. More particularly, the invention relates to a piston pump having a seal leak diagnostic port.

BACKGROUND

Fluid leakage can occur in high-pressure pumps especially after extended use as pump components wear with age. For instance, in liquid chromatography systems, generally, one or more high-pressure pumps take in solvents and deliver a liquid solvent composition to a sample manager, where a sample awaits injection into a mixture. High-performance liquid chromatography (HPLC) systems use high pressure, ranging traditionally between 1,000 to 6,000 psi, to generate the flow required for liquid chromatography in packed columns. In contrast to HPLC, ultra-performance liquid chromatography (UPLC) systems use columns with smaller particulate matter and high pressures that can reach or exceed 20,000 psi to deliver a mobile phase. In many liquid chromatography systems, two or more pumps are employed in a serial or parallel configuration.

In various liquid chromatography applications, a high-pressure seal resides within a gland in either a pump head or a seal wash housing. Over time the seal may wear, causing fluid to leak from the pump head. Diagnostic testing may not be able to identify the failure mode, that is, the cause and source of the leak. For example, the leak may occur at the inside diameter (ID) or the outside diameter (OD) of the high-pressure seal, or at another component such as a check valve or a vent valve.

SUMMARY

In one aspect, the invention features a pump that includes a movable rod, pump head, seal wash housing, fluid channel and diagnostic port. The pump head has an abutment surface and a fluidic chamber to receive the movable rod. The seal wash housing has an abutment surface adjacent to the abutment surface of the pump head and also has a bore through which the movable rod extends into the fluidic chamber. The fluid channel extends, at a first end, from an interface of the abutment surfaces of the pump head and the seal wash housing. The diagnostic port is disposed on either the pump head or the seal wash housing, and is in fluidic communication with a second end of the fluid channel.

In another aspect, the invention features a pump that includes a movable rod, pump head, seal wash housing, seal assembly, fluid channel and diagnostic port. The pump head has an abutment surface and a fluidic chamber to receive the movable rod. The seal wash housing has a first abutment surface that abuts the abutment surface of the pump head and a second abutment surface opposite the first abutment surface. The seal wash housing also has a bore through which the movable rod extends into the fluidic chamber of the pump head and a gland disposed on the bore at the second abutment surface. The seal assembly is disposed in the gland about a circumference of the movable rod such that a seal cavity is defined in the gland between the seal assembly and a surface of the gland. The fluid channel extends, at a first end, from the seal cavity. The diagnostic port is disposed on either the pump head or the seal wash housing and is in fluidic communication with a second end of the fluid channel.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
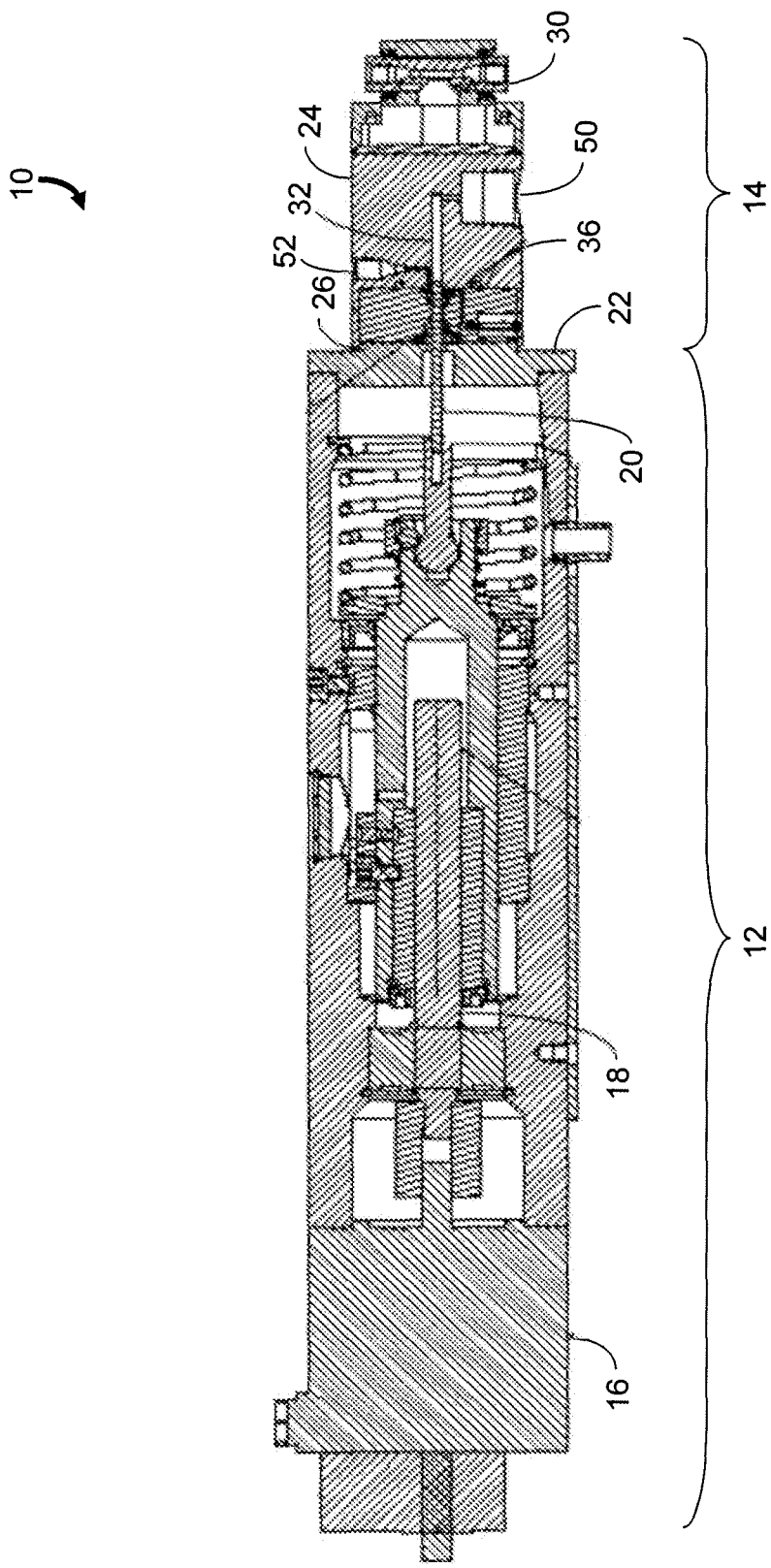
FIG. 1 is a cross-section diagrammatic view of an embodiment of an actuator of a pump used in liquid chromatography applications, the actuator comprising an actuator body and an actuator fluidic assembly having a pump head and seal wash housing.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

Check valves and high pressure seals are common sources of leaks in pumps for high pressure fluid applications such as liquid chromatography. When a pump leak is detected, it can be difficult for users and support personnel to determine if the leak is from a check valve or from a high pressure seal. Consequently, disassembly of at least a portion of the pump may be required to identify the specific cause of the leak.

In brief overview, the invention relates to a pump having a diagnostic port that enables users and support personnel to efficiently diagnose the source of a pump leak. The diagnostic port is monitored either visually or with a pressure or liquid detection sensor. In one embodiment, fluid detected at the diagnostic port corresponds to a leak around a circumference defined at the OD of the high pressure seal. In another embodiment, fluid detected at the diagnostic port corresponds to a leak around the plunger at the ID of the high pressure seal. In still another embodiment, two diagnostic ports are provided, allowing separate determinations of leaks sourced from the OD and the ID of the high pressure seal. The various embodiments can eliminate the need to disassemble the pump assembly to determine the source of certain leaks. Thus the effort required to diagnose and repair the pump assembly can be substantially reduced, and fewer misdiagnosed components are ordered or replaced.

Actuators described herein can be employed in high-pressure reciprocating and rotary applications, such as are commonly used in liquid chromatography. The actuators include an actuator assembly having a pump head coupled to a seal wash housing, a gland in either the pump head or seal washing housing, and a high-pressure seal assembly disposed within the gland. The pump head has an inlet port and an outlet port, each port being in fluidic communication with a chamber. Movement of a plunger within the chamber draws fluid into the chamber through the inlet port and pumps the fluid out of the chamber through the outlet port.

Figure 2:
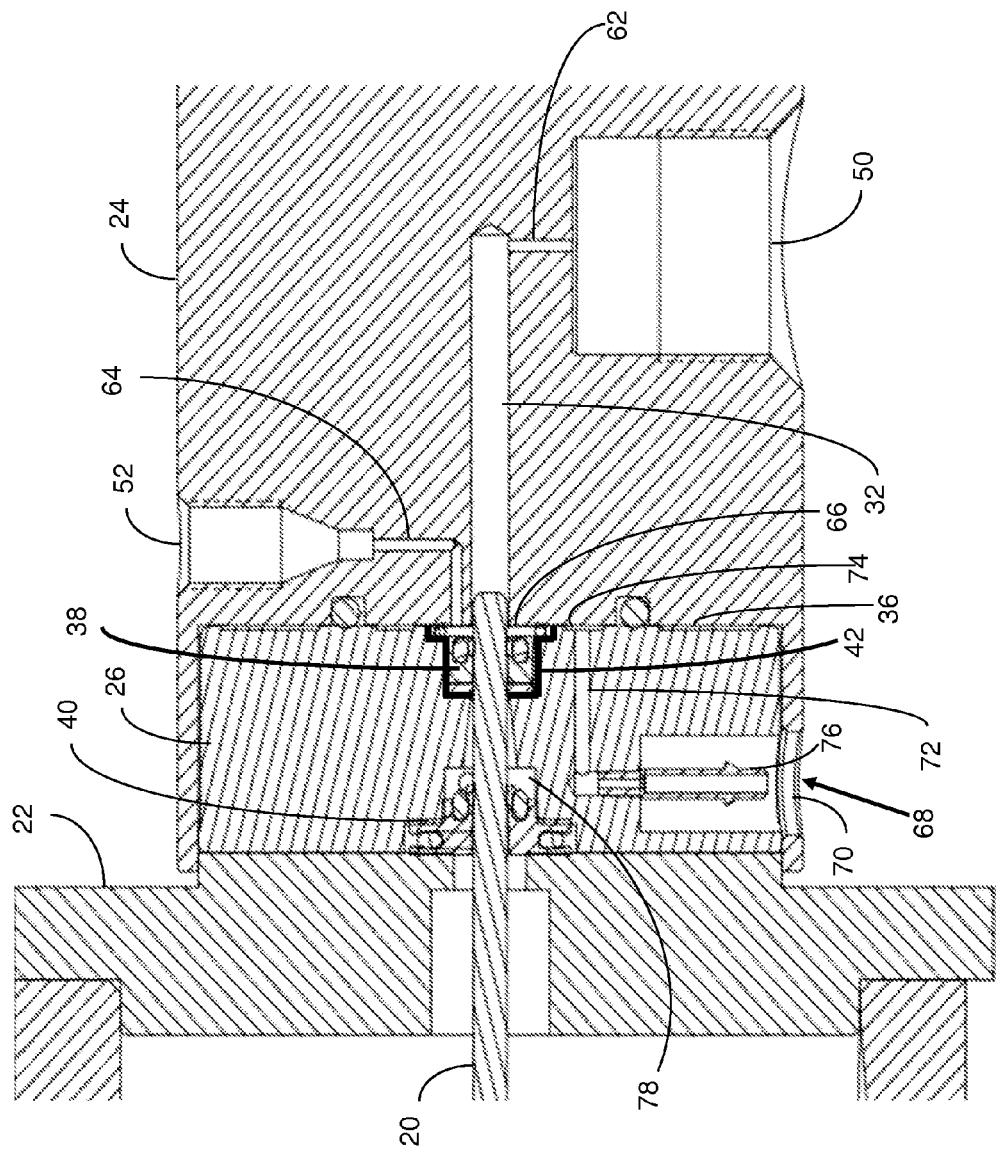
FIG. 2 is an enlarged cross-sectional view of a portion of the actuator fluidic assembly of FIG. 1 that includes the pump head, seal wash housing, and low-pressure and high-pressure seal assemblies.

FIG. 1 shows an embodiment of an actuator 10 having a main actuator body 12 connected to an actuator fluidic assembly 14 and FIG. 2 shows an enlarged view of a portion of the actuator fluidic assembly 14. The main actuator body 12 includes a motor 16 and a drive mechanism 18 mechanically linked to a plunger 20. Although described in connection with reciprocating plungers, the fluidic outlet mechanisms described herein can also be used in actuators with rotary shafts, such as a shaft that rotates and turns a rotor fitted to a stator. The term "rod" is used herein to broadly encompass plungers, shafts, rods, and pistons, whether reciprocating or rotary. The support plate 22 is secured to main actuator body 12.

The actuator fluidic assembly 14 includes a pump head 24 and a seal wash housing 26, both secured to the other side of the support plate 22, opposite the main actuator body 12. The pump head 24 has a counter bore or pocket at one end adapted to receive and align the seal wash housing 26. A pressure transducer 30 is secured to the other end of the pump head 24. The pressure transducer 30 allows the internal pressure of the pump head 24 to be monitored throughout the operation of the actuator 10.

The pump head 24 includes a chamber 32, a bore opening (not visible), and a seal wash housing abutment surface 36 surrounding the bore opening. The plunger 20 extends through the seal wash housing 26 and the bore opening of the pump head 24 into the chamber 32. The seal wash housing 26 provides a compartment to purge fluid and wash the plunger 20 of any particulate that may form on the plunger surface. A high-pressure seal assembly 38 and low-pressure seal assembly 40 serve to contain fluids within their appropriate quarters; the high-pressure seal assembly 38 keeps fluid at a pressure up to or greater than 20,000 psi from leaking into the seal wash housing 26 and other unwanted areas of the pump head 24, and the low-pressure seal assembly 40 keeps the wash fluid in the seal wash compartment. In this embodiment, the high-pressure seal assembly 38 resides within a gland 42 in the seal wash housing 26. The pump head 24 further includes an inlet port 50 and an outlet port 52 through which fluid is received and discharged, respectively. The inlet port 50 joins the chamber 32 at the chamber's remote end, whereas the outlet port 52 is in fluidic communication with the chamber's other end through a seal cavity 66.

In one embodiment, the actuator 10 is one of two independently controllable actuators of a binary solvent manager (BSM) pump. The two actuators are connected in series; one actuator, called the primary actuator, transfers solvents drawn from its chamber 32 to the other actuator, called the accumulator. The intake of fluid occurs in response to the plunger of primary actuator moving within the chamber in a rearward direction and the transfer of pressurized fluid to the accumulator occurs in response to the plunger of primary actuator moving in a forward direction. Closure of an inlet check valve (not shown) ensures expulsion of the pressurized fluid from the chamber through outlet port, rather than through the inlet port. The accumulator delivers the solvent composition to other downstream components of the liquid chromatography system. An example implementation of a BSM pump is the ACQUITY UPLC Binary Solvent Manager, manufactured by Waters Corp. of Milford, Mass.

After extended use, it is common for the seal assemblies 38 and 40 to exhibit wear and eventually fail. Diagnostic testing of conventional pumps used for liquid chromatography may be insufficient for identifying the source of a leak, for example, whether a leak originates at the ID or OD of the seal assembly 38 or 40, a check valve or a vent valve.

Figure 3A:
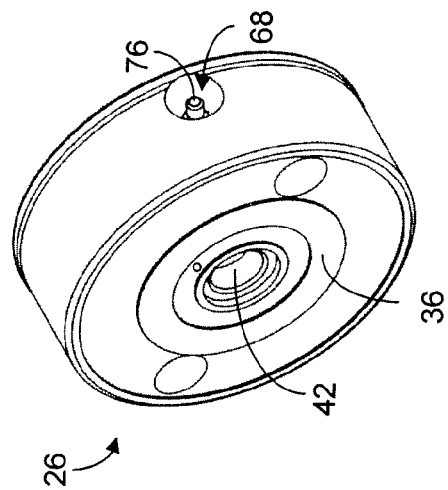
FIGS. 3A and 3B are exploded views of a portion of the actuator fluidic assembly shown in FIG. 1 that show the pump head, seal wash housing and high-pressure seal assembly.
Figure 3A:
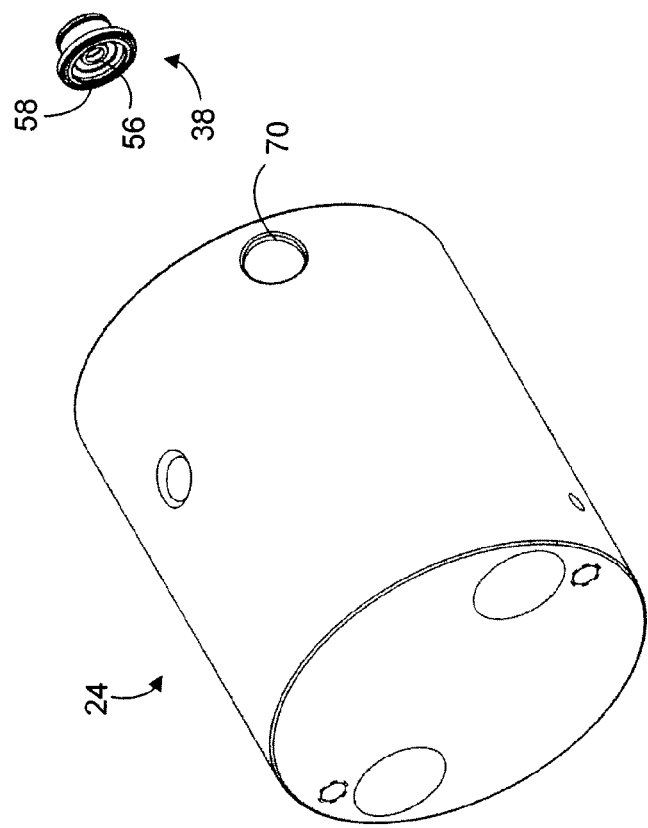
Figure 3B:
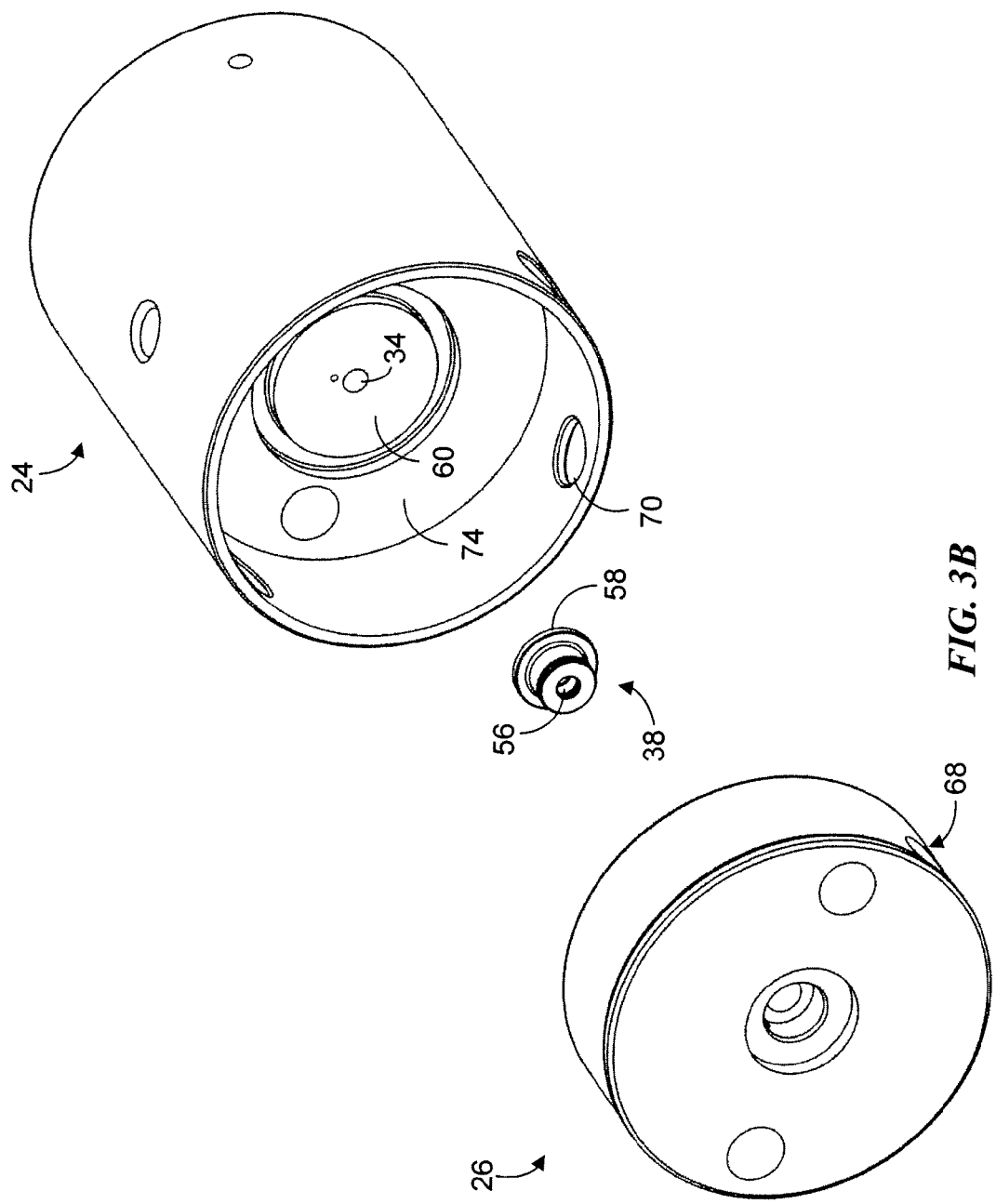

FIGS. 3A and 3B are exploded views of a portion of the actuator of FIG. 1. Referring to FIG. 2 and FIGS. 3A and 3B, a diagnostic port 68 provides users a direct visual means to determine the presence of a leak about the OD of the high-pressure seal assembly 38 such that fluid escaping from the seal cavity 66 can be detected. The diagnostic port 68 includes an opening 70 in the body of the pump head 24 to expose one end of a fluid channel 72 that extends through the seal wash housing 26. The other end of the fluid channel 72 terminates at the interface 74 between the seal wash housing abutment surface 36 and the sealing surface 60 of the pump head 24 outside the region where the seal assembly 38 abuts the sealing surface 60. The location of the diagnostic port 68 at the lower portion (i.e., near or on the bottom) of the pump head 24 and seal wash housing 26 allows gravity to assist the flow of fluid; however, in alternative embodiments, the diagnostic port 68 is located on the side or top of the pump head 24. Preferably, the diameter of the fluid channel 72 is small (e.g., less than 0.020 in. diameter) so that the time for fluid to flow through the channel 72 is brief, thereby providing for quicker detection of a leak.

The fluid channel 72 terminates at a coupling 76 in the diagnostic port 68. The illustrated coupling 76 is a barbed fitting that allows various forms of tubing or other conduit to be attached although other types of fluid couplers can be used. The tubing conducts leaking fluid from the pump head 24 to a remote location. Transparent flexible tubing can be used so that the determination of a leak can be made by observing fluid in the tubing, thus avoiding the need for direct visual inspection of the diagnostic port 68. Preferably, the inner diameter of the flexible tubing is small (e.g., less than 0.020 in.) so that the linear movement of fluid within the tubing is increased for a given leak flow rate, allowing for an easier determination of an occurrence of a leak.

In some embodiments, the tubing is coupled to a pressure sensor or a liquid detection sensor to allow a fluid leak to be determined without reliance on visual observation. In alternative embodiments, the pressure sensor or liquid detection sensor is mounted or secured directly to the diagnostic port 68 or coupling 76. In one example, a pressure sensor is used to detect a pressure increase or "spike" resulting from the transfer of fluid past the seal assembly 38. In another example, a liquid detection sensor includes an optical source and optical detector configured to sense fluid in the tubing. A signal from the optical detector has different states according to whether air or fluid is present in the tubing between the optical source and the optical detector.

In the embodiments described above, the diagnostic port 68 is configured for determining the occurrence of an OD leak of the high pressure seal assembly 38. In alternative embodiments, a diagnostic port can be provided to assist in detecting a leak around the plunger of the high pressure seal assembly 38. More specifically, a fluid channel is provided from the seal cavity 78 (FIG. 2) of the low pressure seal assembly 40 to a diagnostic port on the outside of the seal wash housing 26 through an opening in the pump head 24 (similar to opening 70 for the OD leak diagnostic port 68). If fluid leaks between the ID portion 56 of the seal assembly 38 and the plunger 20, the fluid will enter the seal cavity 78 and will be detectable as an oscillation in the fluid level of a conduit coupled to the ID leak diagnostic port.

While the invention has been shown and described with reference to specific embodiments, it should be understood by those skilled in the art that various changes in form and detail may be made therein without departing from the spirit and scope of the invention as recited in the accompanying claims. By way of examples, in the various embodiments described above with respect to FIG. 2, the fluid channel 72 and diagnostic port 68 are provided in the seal wash housing 26. In alternative embodiments, the fluid channel is provided in the body of the pump head 24 and the diagnostic port is provided on the outer surface of the pump head 24.

What is claimed is:

1. A pump comprising:
   a seal wash housing having an abutment surface, a surface opposite to the abutment surface, a gland extending from the abutment surface and a bore extending from the gland to the surface opposite the abutment surface;
   a pump head having an abutment surface adjacent to the abutment surface of the seal wash housing, a fluidic chamber extending at one end from the abutment surface of the pump head, an inlet port in fluidic communication with the fluidic chamber and an outlet port;
   a movable rod disposed in the bore and configured for axial movement within the fluidic chamber;
   a seal assembly disposed in the gland of the seal wash housing, the seal assembly having a first sealing surface having an inner diameter and being in sealing engagement with a surface of the movable rod, the seal assembly having a second sealing surface having an outer diameter and being in sealing engagement with a portion of the abutment surface of the pump head adjacent to the gland, wherein a seal cavity is defined between the seal assembly and the abutment surface of the pump head that is inside the outer diameter of the second sealing surface, the seal cavity defining a portion of a fluidic path that couples the fluidic chamber to the outlet port; and
   a fluid channel having a first end at an interface of the abutment surfaces of the seal wash housing and the pump head outside the outer diameter of the second sealing surface, and having a second end disposed at a diagnostic port on an outer surface of the pump head or the seal wash housing.

2. The pump of claim 1 wherein the fluid channel is inside the seal wash housing.

3. The pump of claim 1 wherein the fluid channel is inside the pump head.

4. The pump of claim 1 wherein at least a portion of the fluid channel is disposed in a direction to improve a flow of fluid by gravity from the interface of the abutment surfaces of the seal wash housing and the pump head to the diagnostic port.

5. The pump of claim 1 further comprising a liquid sensor in fluidic communication with the diagnostic port.

6. The pump of claim 1 further comprising a pressure sensor in fluidic communication with the diagnostic port.

7. The pump of claim 1 wherein the diagnostic port comprises a coupling in fluidic communication with the second end of the fluid channel and configured to receive a conduit to conduct fluid between the fluid channel and a location remote to the pump.

\* \* \* \* \*